United States Patent [19]

Boehringer

[11] 4,182,366
[45] Jan. 8, 1980

[54] POSITIVE END EXPIRATORY PRESSURE DEVICE

[76] Inventor: John R. Boehringer, 427 Parkview Dr., Wynnewood, Pa. 19096

[21] Appl. No.: 647,340

[22] Filed: Jan. 8, 1976

[51] Int. Cl. ............................................... F16K 31/12
[52] U.S. Cl. .................................... 137/510; 137/514; 137/514.5
[58] Field of Search ...................... 137/510, 514, 514.5, 137/514.7

[56] References Cited

U.S. PATENT DOCUMENTS

| | | | |
|---|---|---|---|
| 1,616,032 | 2/1927 | Duffy | 137/510 |
| 1,871,535 | 8/1932 | Lattner | 137/510 X |
| 2,639,194 | 5/1953 | Wahlin | 137/510 X |
| 2,888,947 | 6/1959 | Montgomery | 137/510 X |
| 2,918,082 | 12/1959 | Pinke | 137/510 X |
| 3,043,333 | 7/1962 | Kugler | 137/510 X |
| 3,294,114 | 12/1966 | Birkemeier | 137/510 |
| 3,419,039 | 12/1968 | Monnich | 137/510 |
| 3,474,816 | 10/1969 | Burgess | 137/510 X |
| 3,550,617 | 12/1970 | Johnson | 137/514.5 |

FOREIGN PATENT DOCUMENTS 1208796  10/1970  United Kingdom ..................... 137/510

Primary Examiner—Harold W. Weakley
Attorney, Agent, or Firm—Paul & Paul

[57] ABSTRACT

A diaphragm divides a chamber into two segments, the first of which includes an air input port and an outlet port formed by a tube which contacts the diaphragm. On the other side of the diaphragm, a variably adjustable spring actuated piston urges the diaphragm to closure against the outlet port. Incoming air pressure deflects the diaphragm away from the outlet port against the spring and air compression, to allow predetermined exhaust air flow. A valved opening behind the diaphragm provides safety against diaphragm tear and malfunction.

7 Claims, 5 Drawing Figures

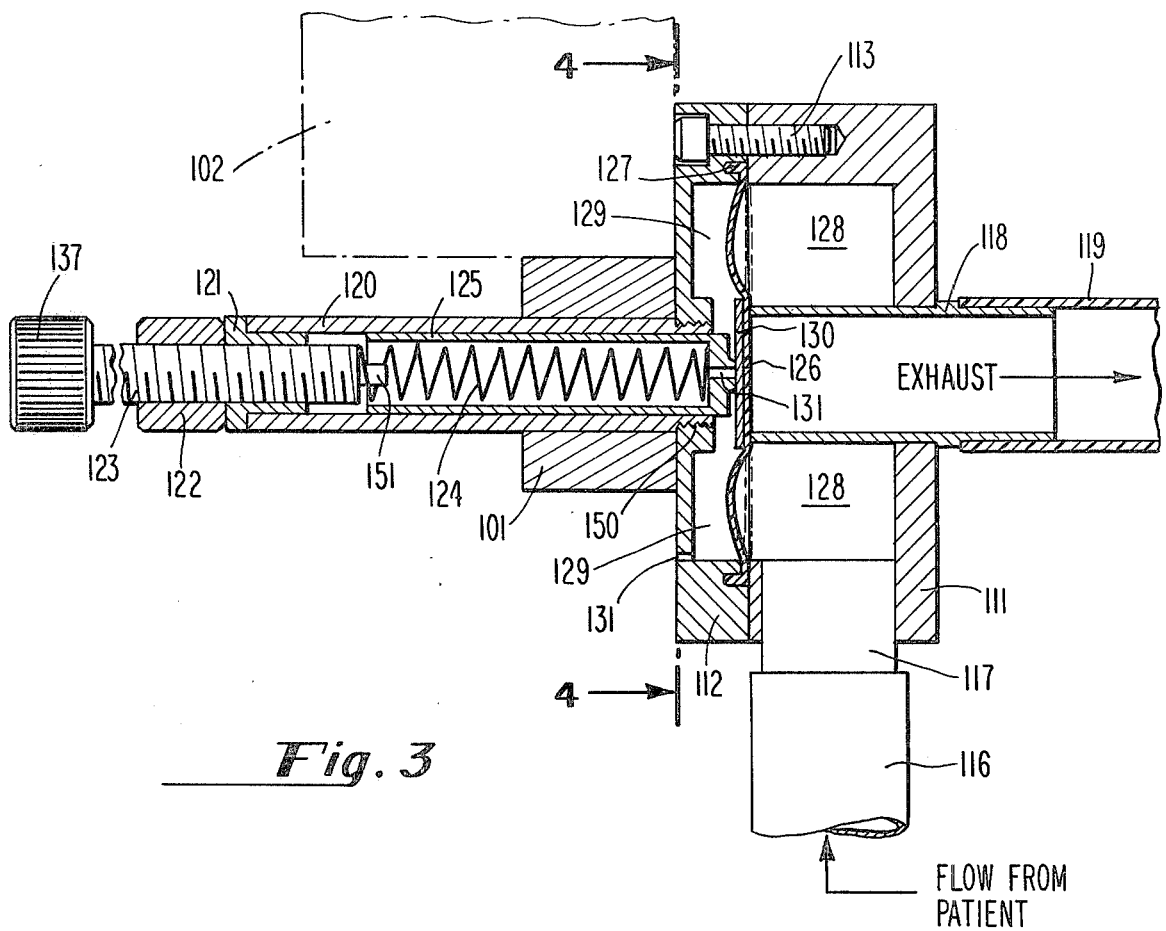
*Fig. 3*
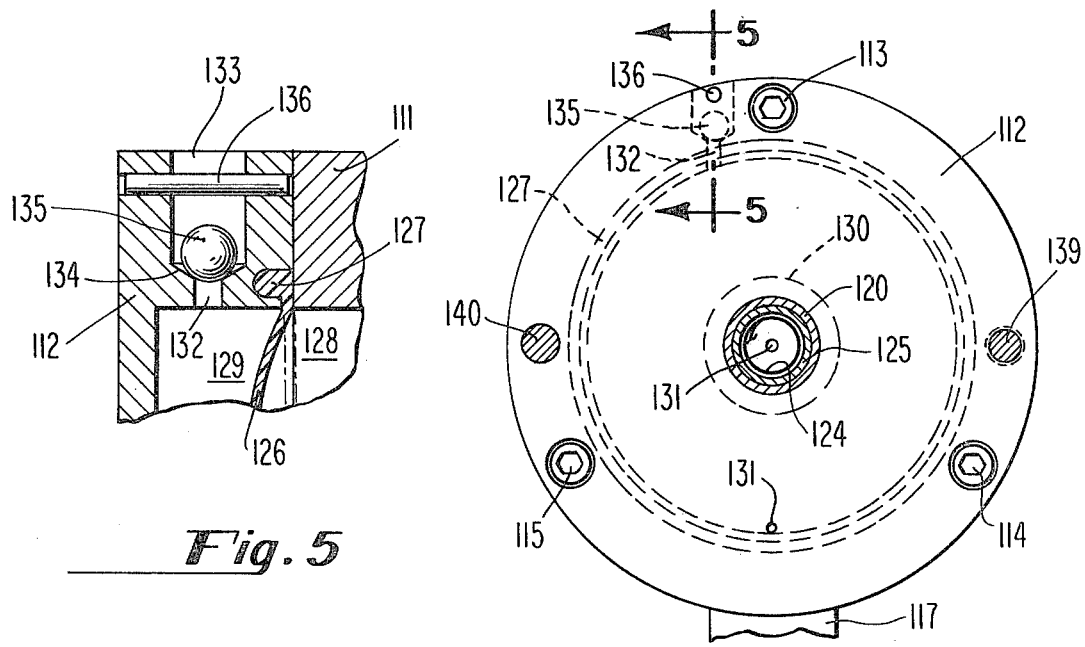
*Fig. 5*
*Fig. 4*

POSITIVE END EXPIRATORY PRESSURE DEVICE

BACKGROUND OF THE INVENTION

This invention relates to valve apparatus, and more particularly to the class of valves commonly known as positive end expiratory pressure devices.

Positive end expiratory pressure (PEEP) has become a mainstay in the treatment of patients with respiratory failures. In such treatment, there is provided a carefully structured and controlled back pressure to the patient, thereby forcing the patient to exert a clinically desirable amount of respiratory effort. Typically, regulation of the pressure characteristics of the PEEP device allows for progressive, increases of lung effectiveness and capacity of the patients.

Increasing use of PEEP devices and therapy has yielded rather sharp performance requirements, not only from the primary standpoint of effectiveness and safety to the patient, but also with respect to ease and convenience of use. From the standpoint of patient effectiveness and safety, it is desirable that PEEP devices provide for a broad pressure range, including relatively high pressures in the 20 to 30 centimeters H$_2$O range, without impairment of effectiveness at any given operating point. Further, it is desirable that the pressure characteristics of the device be relatively independent of the air flow rate, such that the therapy may be utilized even with patients with severe pulmonary disfunction. Equally important, the valve response time to exerted pressure changes should be as quick as possible, to avoid transmittal back of undue transient pressures to the patient, and vibration and flutter of the pressure are to be similarly avoided. With respect to convenience and ease of use, it is desirable that the apparatus be sterilized easily, provide as close to infinite adjustability as possible, and allow for simple and accurate determination by the doctor or therapist of the current operational condition of the device.

The present invention has as its primary objects provision of positive end expiratory pressure devices which satisfy the above considerations as closely as possible. It is a further object of the present invention to provide such devices which may be conveniently used separately as a ventilator on constant flow circuits commonly known as constant positive air way pressure (CPAP) apparatus.

SUMMARY OF THE INVENTION

The present invention provides for virtually infinitely variable positive end pressure over a broad pressure range, with virtual independence to flow rates, by utilizing deflection of a diaphragm against predetermined and controlled back pressure of an air reservoir and a spring actuated piston.

In an illustrative embodiment, a housing is divided into two cavities by a soft rubber diaphragm; one of the cavities is provided an inlet port and an outlet port terminating against the undeflected diaphragm. A spring actuated piston penetrates the other cavity and urges the diaphragm against the outlet port, and that cavity is provided with controlled ventilation to combine with the spring actuated piston for further contribution to resistance to diaphragm deflection. As the inlet pressure increases, the diaphragm is deflected correspondingly, and to the extent that resistive force to the deflection is overcome, a discontinuity is created and/or maintained at the outlet port for exhaust flow. A valved opening is provided behind the diaphragm for safety purposes, which opening is closed during normal operation, but which pops open in the eventuality of a diaphragm tear and a consequent back pressure situation which tends to lock the outlet port closed. A pressure gauge is coupled to the device, and provides direct reading of operative pressures.

DESCRIPTION OF THE DRAWINGS

FIG. 3 shows a central cross-section of the FIG. 1 device which illustrates the operation of the principles of the present invention.

FIG. 4 shows a partial cutaway of the FIG. 3 apparatus, and

FIG. 5 shows a partial section of FIG. 4 for purposes of illustrating a preferred safety valve configuration.

DETAILED DESCRIPTION

Figure 2:
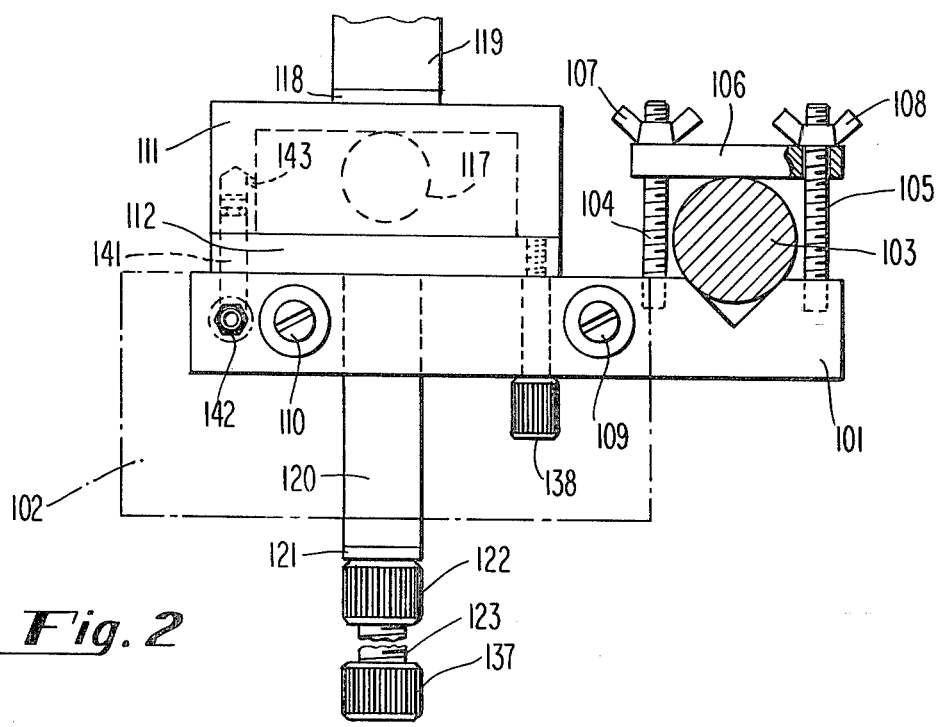
FIG. 2 shows a top view of the same.

Referring to the drawings, there is shown a preferred embodiment of the principles of the present invention. All of the apparatus shown is mounted on a rugged bracket 101, which through screws 104 and 105, wing nuts 107 and 108, and a mounting plate 106 may be conveniently fastened to a pole 103 such as those utilized for mounting intravenous apparatus, or any other such convenient place. The configuration shown allows for safe and secure attachment to poles 103 of widely disparate sizes, and the mounting plate 106 is advantageously configured as a latch, having a hole for screw 104 and a notch for screw 105. Quick and easy mounting is thereby facilitated by pivotable use of the plate 106 in conjunction with wing nuts 107 and 108.

A pair of screws 109 with associated washers are utilized to mount a meter 102 to the bracket 101. The meter 102, provides a direct reading of the present pressure in the device, such as by deflection of a pointer 144 along suitable scale indicia 145. Neither the precise readout mode nor the precise embodiment for the meter 102 is not crucial to the principles of the present invention.

Figure 1:
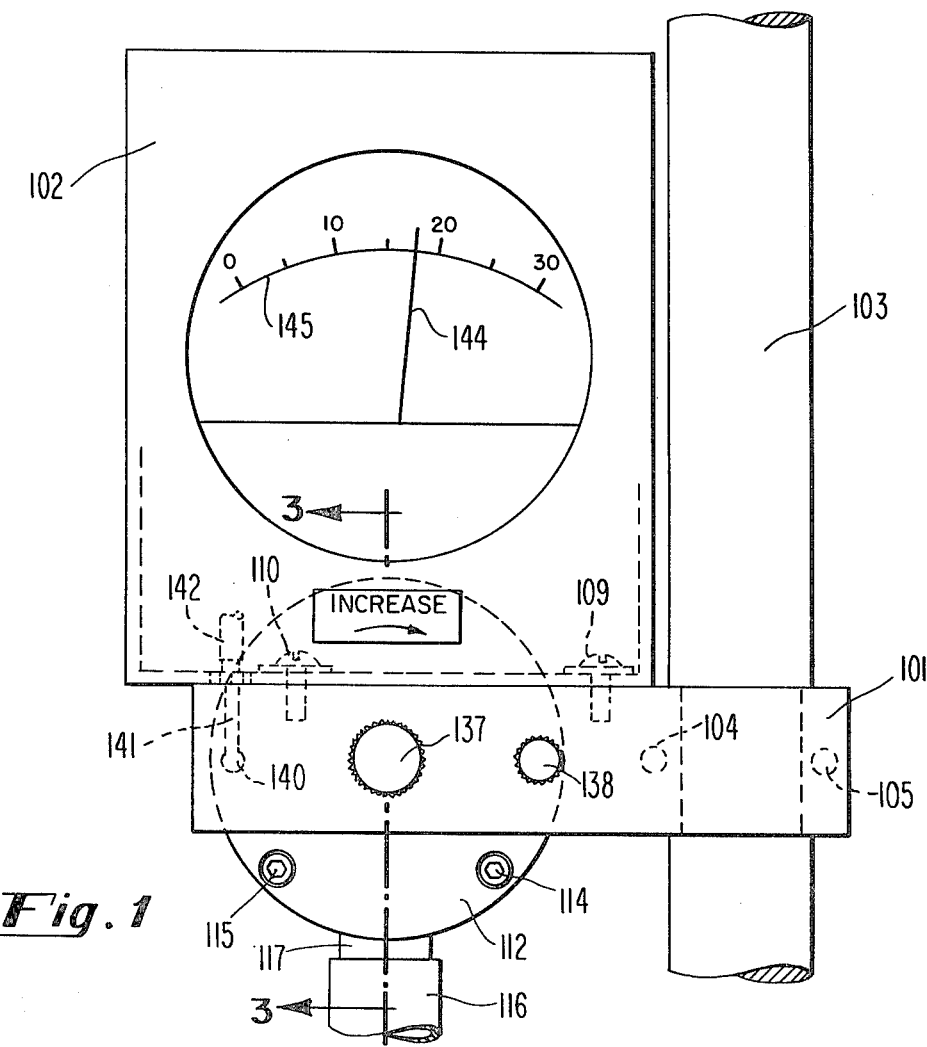
FIG. 1 shows a frontal, external view of a preferred embodiment of the present invention.

Referring particularly to FIG. 3, which shows a central cross-section of the FIG. 1 apparatus, operation of the principles of the present invention may be most clearly seen. Front and back sections 112 and 111, respectively, together form a valve chamber, which is divided into first and second cavities, 128 and 129 respectively, by a soft rubber diaphragm 126. Advantageously, the diaphragm 126 includes a flange 127 around its periphery. Front segment 112 of the housing defines a though for engaging the flange 127, and closure of set screws 113, 114, and 115 seals the front and back segments 112 and 111 of the housing against one another. In turn, the cavities 128 and 129 within the chamber formed by the housing are isolated from one another.

The back cavity 128 is provided with an inlet 117 through which flow is received from the patient, advantageously by an overlap connection with a tube or the like 116. Preferably, the cavities 128 and 129 are generally cylindrical in configuration, and preferably also the inlet port 117 is located in the lowermost portion of the cavity 128. An exhaust, or outlet port is provided by means of a tubular element 118 which penetrates the rear segment 111 of the housing along the axis of cavity 128, and extends therein to the stationary position of the diaphragm 126. That is, in the quiescent state, the diaphragm 126 is in the position shown in phantom in FIG. 3, and the tubular element 118 extends into cavity 128 to contact the diaphragm at that point. Exhaust from element 118 is conducted by an overlapping tube 119, or the like.

A cylinder 120 penetrates the bracket 101 and is mounted in threaded engagement at 150 with the front portion 112 of the housing of the valve. The cylinder 120 terminates at the end opposite the bracket 101 in a sealed connection 121, which may be a discrete part as shown, or which alternatively may be integral with the cylinder 120. A screw 123 operable by a knurled knob 137 penetrates the termination part 121 of cylinder 120, and is also provided with a lock nut 122 for securing its position relative to cylinder 120, as desired. Within cylinder 120 is an elongated piston 125 which is slidable within the cylinder 120 and which advantageously is hollow as shown. A spring 124 is provided within the piston 125 between the screw 123 and end of the piston which penetrates cavity 129. The spring 124 therefore provides predetermined force, calibrated in accordance with the characteristics of the spring itself and the position of screw 123, to urge the piston 125 within cylinder 120 in the direction of the diaphragm 126.

A rigid disk 130, advantageously composed of metal and having a diameter greater than that of the tubular element 118 is interposed between the piston 125 and the diaphragm 126 by securement to the diaphragm, whereby the spring force from the piston 125 tends to sealably urge the soft rubber diaphragm 126 against the outlet port of element 118. The piston 125 is further provided with a port 131 at its contact point with the disk 130. The size of the port 131 and the clearance of the piston 125 with the inner walls of cylinder 120 are calibrated to provide predetermined air flow characteristics, as described hereinafter. Further, the cavity 129 is provided with a bleed hole 131 for controlled escape of air therefrom.

The apparatus of FIG. 3 functions as follows. With no pressure provided from the patient into cavity 128, the piston 125 is positioned as shown, and the diaphragm 126 is unstretched as shown in phantom. As pressure is applied from the patient, the diaphragm begins to deflect as shown in FIGS. 3 and 5. At this point, the back pressure provided to the patient results somewhat from the resistance of the soft rubber diaphragm 126. As the diaphragm 126 is deflected its resistance to further stretching tends to become larger than the resistive force of piston 125 against the metal disk 130, and the piston 125 is progressively translated away from the outlet element 118. During such operation, the damping force from compression of air in chamber 129 continues to be a factor, but two further significant factors are provided. First, the spring 124 itself provides a component of resistance to translation of the piston 125. Equally significant, however, is the dash-pot effect provided by air within the hollow piston 125. That is, as the pressure on the diaphragm 126 is increased, port 131 of piston 125 is closed by disk 130, and compression of air within piston 125 is relieved only by the predetermined escape of air between piston 125 and cylinder 120 into the cavity 129. This combination of forces tends to provide a rather stiff dash-pot effect, the precise extent of which is adjustable by operation of the screw 123.

During the entire time in which the piston 125 is displaced from the closure position shown in FIG. 3, the soft rubber diaphragm 126 conforms to and travels with the disk 130, thereby providing continuity between the inlet 117 and exhaust 118 portions of the device. The cylindrical configuration of cavity 128 together with the coaxial location of exhaust element 118 insures relatively unimpeded flow from inlet through exhaust, and accentuates the flow independence of the device. Further, local flutter such as is often experienced in the use of thin sheet rubber diaphragms in pneumatic instruments is prevented by the disk 130, which is fixed to the diaphragm 126 as shown.

As pressure is relieved in the chamber 128, port 131 of piston 125 is opened, allowing the spring 124 to urge the piston 125 rapidly to follow the diaphragm 126. This creates a differentially damped system thus reducing the tendency to oscillate. Air flow back into the chamber 129 is facilitated by the bleed hole 131. The configuration and orientation shown in the drawings for the inlet port 117 allows for safe and automatic self draining of the device. Further, undesirable accumulation of liquid in the chamber of piston 125 will drain both through the clearance between piston 125 and cylinder 120, and to a lesser extent through the port 131 in the piston.

An important safety feature is shown in FIGS. 4 and 5, which involves a valved opening 132 and 133 which opens the upper portion of cavity 129 to the atmosphere. A ball of predetermined weight and specific gravity 135 and a stop 136 are provided as shown, and the upper 133 and lower 132 portions of the opening together provide a frustoconical seat 134 for the ball 135. The opening 132 and 133 is provided only for purposes of malfunction such as a rupturing of the diaphragm 126 in which the inlet pressure flow from the patient would be communicated through the rupture and provide sealing force against the exhaust outlet 118. Thus, in normal operation, the ball 135 is seated at 134 and the device functions as described hereinbefore, but in the event of the accelerated pressures occuring upon diaphragm rupture and back sealing against the exhaust, the ball 135 is raised within the upper portion 133 of the opening, and dangerous pressure against the patient is relieved.

In order to monitor the operation of the valve, channel 140 and 141 is provided in the bracket 101 and the housing portions 111 and 112 and is coupled at a small tap 143 to the chamber 128. The meter 102 may therefore be directly connected at 142 continuously and directly to monitor pressure in cavity 128. As set forth hereinbefore, the construction of the meter 102 is not critical to the principles of the present invention. For example, the meter 102 may be embodied by any of the class of diaphragm-magnetic drive meters commercially available, such as the one sold under the trade name "Dwyer Magne-helic".

It will be apparent from the foregoing that the embodiment set forth is ideally suited for ease of assembly, or disassembly for sterilization of desired parts. Also, the threaded engagement of the cylinder 120 with the housing, together with a separate locking screw 138 into bracket 101 and the front portion 112 of the housing insures proper registry of the meter input 142 with the pressure tap 143. It will further be apparent that the ease of assembly and disassembly allows for use of a variety of springs 124, each having specific characteristics and thereby yielding corresponding operable pressure ranges for the device. Likewise, the diaphragm 126 may periodically be conveniently replaced, as desired.

The foregoing is submitted as illustrative of the present invention, and it is to be understood that numerous alternative embodiments will occur to those of ordinary skill in the art without departure from the spirit or scope of the principles thereof.

I claim:

1. Positive end pressure valve apparatus comprising:
   (a) a flexible diaphragm;
   (b) housing means forming a chamber therein, said chamber being divided into segments by said diaphragm, said housing having an inlet port and an exhaust port penetrating a first one of said segments, said exhaust port being defined by a hollow protuberance into said first segment opening against said diaphragm in an undeflected condition; and
   (c) piston and cylinder means communicating with said housing means into the second of said segments, said cylinder being closed at one end and opening directly into said second segment at its other end, said piston travelling within said cylinder between said diaphragm and said one end, and having an elongated, hollow, cylindrical configuration, open facing said one end and closed but for a port at the end opposite said one end, said port connecting said second segment with the interior of said piston, said piston and said cylinder having predetermined clearance for further communication of said second segment with the interior of said piston, said diaphragm and said piston offering predetermined force to pressure at said inlet port by air compression and flow within and between said second segment and said piston and cylinder means;
   (d) whereby pressure exerted at said inlet port deflects said diaphragm and displaces said piston in opposition to said pressure exerted, creating a discontinuity between said diaphragm and said protuberance for exhaust flow between said inlet and exhaust ports.

2. Apparatus as described in claim 1 wherein said piston and cylinder means comprises a piston slidably mounted in a cylinder communicating with said second segment, and spring means, urging said piston against said diaphragm opposite said protuberance, said spring providing resistance to said pressure exerted at said inlet port, in calibrated conjunction with said forces of air compression and flow within and between said second segment and said piston and cylinder means.

3. Apparatus as described in claim 2 wherein said diaphragm is generally circular, said chamber is cylindrical, said protuberance is generally tubular and coaxial with said chamber and said piston and cylinder are coaxial with said chamber.

4. Apparatus as described in claim 3 and further including a disk, larger than said opening of said protuberance but smaller than said diaphragm, interposed between said piston and said diaphragm, wherein said port in said piston is smaller than said disk and is located at the contact location of said piston and said disk.

5. Apparatus as described in claim 3 wherein said spring means includes adjustable means for variably biasing said predetermined force.

6. Apparatus as described in claim 3 wherein the axis of said cylindrical chamber is generally horizontal, and wherein said inlet port penetrates the lower portion of said chamber.

7. Apparatus as described in claim 1 wherein said housing means further defines a valved safety outlet for said second segment of said chamber, said outlet being closed during normal operation and opening from pressure buildup occasioned by a tear of said diaphragm and lockup of said outlet port.

* * * * *

UNITED STATES PATENT OFFICE
CERTIFICATE OF CORRECTION

Patent No. 4,182,366          Dated January 8, 1980

Inventor(s) John R. Boehringer

It is certified that error appears in the above-identified patent and that said Letters Patent are hereby corrected as shown below:

Claim 7, line 34, after "said chamber" delete --, said outlet being closed during normal operation and opening from pressure buildup occasioned by a tear of said diaphragm and lockup of said outlet port --

Signed and Sealed this

Thirteenth Day of May 1980

[SEAL]

Attest:

SIDNEY A. DIAMOND

Attesting Officer      Commissioner of Patents and Trademarks